(12) United States Patent
Dumesic et al.

(10) Patent No.: US 7,960,592 B1
(45) Date of Patent: Jun. 14, 2011

(54) PRODUCTION OF METHYL-VINYL KETONE FROM LEVULINIC ACID

(75) Inventors: James A. Dumesic, Verona, WI (US); Ryan M. West, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 12/685,887

(22) Filed: Jan. 12, 2010

(51) Int. Cl.
  *C07C 45/65* (2006.01)
(52) U.S. Cl. ...................................................... 568/397
(58) Field of Classification Search .................... 568/397
  See application file for complete search history.

(56) References Cited

U.S. PATENT DOCUMENTS

| | | |
|---|---|---|
| 2,809,203 A | 10/1957 | Leonard |
| 3,476,803 A | 11/1969 | Pine |
| 5,608,105 A | 3/1997 | Fitzpatrick |
| 2005/0210738 A1 | 9/2005 | Manzer |

FOREIGN PATENT DOCUMENTS

| | | | |
|---|---|---|---|
| GB | 601922 | * | 10/1947 |
| WO | WO 2005/097723 A2 | | 10/2005 |
| WO | WO 2008/142127 A1 | | 11/2008 |
| WO | WO 2009/007391 A1 | | 1/2009 |

OTHER PUBLICATIONS

G. Cavinato and L. Toniolo, (1990), Levulinic Acid Synthesis Via Regiospecific Carbonylation of Methyl Vinyl Ketone or of Its Reaction Products With Hydrochloric Acid or an Aleanol or of a Mixturjz of Acetone With a Formaldehyde Precursor Catalyzed by a Highly Active Pd-Hcl System, *Journal of Molecular Catalysis*, 58:251-267.

O.L. Chapman and C.L. McIntosh, (1971), Photochemical Decarbonylation of Unsaturated Lactones and Carbonates, *Journal of the Chemical Society [Section] D: Chemical Communications*, pp. 383-384.

R.H. Leonard, (1956), Levulinic Acid as a Basic Chemical Raw Material, *Journal of Industrial and Engineering Chemistry*(Washington, D. C.), 48:1331-1341.

W.F. Maier, W. Roth, I. Thies and P.V.R. Schleyer, (1982), Gas Phase Decarboxylation of Carboxylic Acids, *Chemische Berichte*, 115:808-812.

NIST Chemistry WebBook (NIST Standard Reference Database No. 69). U.S. Secretary of Commerce 2009, 3 pages.

W. Skorianetz and G. Ohloff,(1975), Cheletrope Reaktion vinyloger Enollactone, *Helvetica Chimica Acta*, 58:1272-1275.

Z.P. XU, C.Y. MOK, W.S. Chin, H.H. Huang, S. Li and W. Huang, (1999), Interconversion and decomposition of furanones, *Journal of the Chemical Society*, Perkin Transactions 2: Physical Organic Chemistry (1999) 725-729.

M. Zviely, R. Giger, E. Abushkara, A. Kern, H. Sommer, H.-J. Bertram, G.E. Krammer, C.O. Schmidt, W. Stumpe and P. Werkhoff, (2002), Application of Chromatographic an Spectroscopic Methods for Solving Quality Problems In Severa Flavour Aroma Chemicals, *Special Publication—Royal Society of Chemistry*, pp. 39-53.

* cited by examiner

*Primary Examiner* — Sikarl A Witherspoon
(74) *Attorney, Agent, or Firm* — Joseph T. Leone, Esq.; DeWitt Ross & Stevens S.C.

(57) ABSTRACT

A method for converting levulinic acid to methyl vinyl ketone is described. The method includes the steps of reacting an aqueous solution of levulinic acid, over an acid catalyst, at a temperature of from room temperature to about 1100 K. Methyl vinyl ketone is thereby formed.

24 Claims, 8 Drawing Sheets

PRODUCTION OF METHYL-VINYL KETONE FROM LEVULINIC ACID

FEDERAL FUNDING

This invention was made with United States government support awarded by the following agencies: U.S. Department of Energy DE-FG02-03ER15468. The United States government has certain rights in this invention.

BACKGROUND

Significant advances have been made in recent years with respect to using heterogeneous catalysts for converting biomass-derived compounds to fuels and chemicals (Kunkel (2008), Chheda (2007), Huber (2007), C. H. Christensen (2008)). These studies deconstruct solid cellulose into smaller molecules that are soluble in various solvents (e.g., water, ionic liquids), thereby allowing transport of these reactants to the active sites on the heterogeneous catalyst, the majority of which are located within the pores of a high-surface area material (Robinson (2004), Zhu (2006)). A difficulty in implementing this strategy is that chemical components used to deconstruct solid cellulose (e.g., sulfuric acid) may alter the performance of heterogeneous catalysts used subsequently to convert the soluble biomass-derived reactants to the desired fuels and/or chemicals. As a result, costly purification steps are required to implement a cascade catalytic process. The present invention is a cascading method to convert cellulose to value-added chemical compounds that addresses this long-felt and unmet need. More specifically, described herein is a method to convert levulinic acid (LA) to methyl-vinyl ketone (MVK) (i.e., but-3-en-2-one, CAS No. 78-94-4) an important industrial intermediate and alkylating agent.

SUMMARY OF THE INVENTION

The primary version of the invention is directed to a method for converting levulinic acid to methyl vinyl ketone. The method comprises reacting a solution comprising levulinic acid, over an acid catalyst, at a temperature of from room temperature to about 1100 K, and in the absence of added molecular hydrogen. The reaction can take place in a batch reactor or a continuous reactor. A continuous reactor is much preferred. It is also preferred that the acid catalyst be a solid acid catalyst.

More specifically, the preferred version of the invention is directed to a method for converting levulinic acid to methyl vinyl ketone. The preferred version of the method comprises reacting in a continuous reactor a solution comprising levulinic acid, over a solid acid catalyst, at a temperature of from room temperature to about 1100 K, and in the absence of added molecular hydrogen, at a temperature of from about 300 K to about 1100 K, a pressure of from about 0.01 bar to about 300 bar, and a weight-hourly space velocity of from about 0.1 $hr^{-1}$ to about 50 $hr^{-1}$.

All percentages, parts and ratios used herein are by weight of the total composition, unless otherwise specified. All such weights as they pertain to listed ingredients are based on the active level and, therefore, do not include solvents or by-products that may be included in commercially available materials, unless otherwise specified. Reaction solutions may be aqueous or non-aqueous.

The catalysts described herein may be used without a support or disposed on an inert or catalytically active support. Any catalyst support now known or developed in the future, without limitation, may be used. Suitable supports include carbon in any form (including nano-particles, "buckyballs," single and multi-wall nanotubes, etc.), silica, titania, alumina, silica/alumina, zirconia, etc., in any form (e.g., spheres, tablets, Raschig rings, and the like), zeolites, etc.

Solid acid catalysts may be used in the present method, including any ceramic acid or acidic molecular sieve such as an acidic zeolite, an aluminosilicate, a titanosilicate, a borosilicate, any mixed oxide such as tungstated zirconia, any phosphated or sulphated catalyst such as sulphated or phosphated metal oxide, or a phosphate or sulphuric acid catalyst such as niobium phosphate, any heteropoly acid, any polyoxymetalate (POM), and any acidic ion exchange resin, as well as any combination or subset of these supported on inert materials such as carbon.

POMs belong to a large class of nanosized metal-oxygen cluster anions. POMs form by a self-assembly process, typically in an acidic aqueous solution and can be isolated as solids with an appropriate counter-cation, for example, $H^+$, alkali metals, $NH_4^+$, and the like.

In the chemical literature, two types of POMs are distinguished based on their chemical composition: isopoly anions and heteropoly anions. These anions may be represented by the general formulae:

| | |
|---|---|
| $[M_mO_y]^{p-}$ | Isopoly anions |
| $[X_xM_mO_y]^{q-}$ ($x \leq m$) | Heteropoly anions |

The "M" moiety is called the addenda atom and the "X" moiety the heteroatom (also called the central atom when located in the center of the polyanion). The distinction between the two groups is frequently artificial, especially in the case of mixed addenda POMs. Thus, as used herein, the term "POM" explicitly refers to both isopoly anions and heteropoly anions. Certain POMs can also be considered heteropoly acids (i.e., strong acids composed of heteropoly anions, with protons as the countercations), and these types of POMs are preferred for use in the present method.

The most common addenda atoms ("M") are molybdenum or tungsten, less frequently vanadium or niobium, or mixtures of these elements in their highest oxidation states ($d^0$, $d^1$). A far broader range of elements can act as the heteroatoms. In fact, essentially all elements of the Periodic Table can be incorporated as the heteroatom in a POM. The most typical for the catalytic POMs described in the prior art are $P^{5+}$, $As^{5+}$, $Si^{4+}$, $Ge^{4+}$, $B^{3+}$, etc. Molybdenum (VI) and tungsten (VI) most readily form POMs due to their favorable combination of ionic radius, charge, and the accessibility of empty d orbitals for metal-oxygen bonding.

A systematic nomenclature of POMs has been developed. It uses a labeling system for the metal atoms and, in some cases, for the oxygen atoms to avoid ambiguity. The resulting names, however, are very long and cumbersome; hence the systematic nomenclature is rarely used for routine purposes. Usually a simplified conventional nomenclature, sometimes even trivial names, are sufficient for reporting and retrieving information in the field. The current simplified nomenclature treats POMs (also referred to as heteropoly anions, polyoxoanions, or polyanions) as quasi-coordination complexes. The heteroatom, if present, is considered as the central atom of a complex, and the addenda moieties as the ligands. In the formulae of heteropoly anions, the heteroatoms are placed before the addenda, and the countercations before the heteroatoms; the heteropoly anion is placed in square brackets and thus separated from the countercations, as illustrated by the following examples:

| | |
|---|---|
| $[SiW_{12}O_{40}]^{4-}$ | 12-tungstosilicate or dodecatungstosilicate |
| $H_3[PMo_{12}O_{40}]$ | 12-molybdophosphoric acid |
| $Na_5[PMo_{10}V_2O_{40}]$ | sodium decamolybdodivanadophosphate |

For simplicity, the countercations and the charge of polyanion and even the oxygen atoms are sometimes omitted; for example, $Na_6[P_2Mo_{18}O_{62}]$ may be abbreviated to $[P_2Mo_{18}O_{62}]$ or simply $P_2Mo_{18}$.

When homogeneous catalysts are used, it is preferred that residual homogenous catalyst from any earlier step in the method is present in a concentration of between 0 and about 2 M, more preferably between 0 and about 0.5 M, and more preferably still between 0 and about 0.1 M.

The various reactions may be conducted under a host of temperature, pressure, and WHSV ranges. While not being limited to these ranges, it is preferred that the various reactions described herein be conducted at a temperature range of from about 300 K to about 1100 K, more preferably from about 350 K to about 800 K, and more preferably still from about 400 K to about 600 K. Reaction temperatures above and below these stated ranges are explicitly within the scope of the method claimed herein. The reactions are preferably conducted at pressures ranging from about 0.1 bar to about 300 bar, more preferably from about 1 bar to about 20 bar, and most preferably from about 1 bar to about 5 bar. Reaction pressures above and below these stated ranges are explicitly within the scope of the method claimed herein. The reactions are preferably conducted at a WHSV of from about 0.1 to about 50 h$^{-1}$, more preferably from about 0.1 to about 30 h$^{-1}$, and most preferably from about 0.1 to about 10 h$^{-1}$. WHSVs above and below these stated ranges are explicitly within the scope of the method claimed herein.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, 5, 6, from 1 to 9, from 3.6 to 4.6, from 3.5 to 9.9, and so forth.

All references to singular characteristics or limitations of the present invention shall include the corresponding plural characteristic or limitation, and vice-versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods of the present invention can comprise, consist of, or consist essentially of the essential elements and limitations of the method described herein, as well as any additional or optional ingredients, components, or limitations described herein or otherwise useful in synthetic organic chemistry.

DETAILED DESCRIPTION OF THE INVENTION

Figure 1:
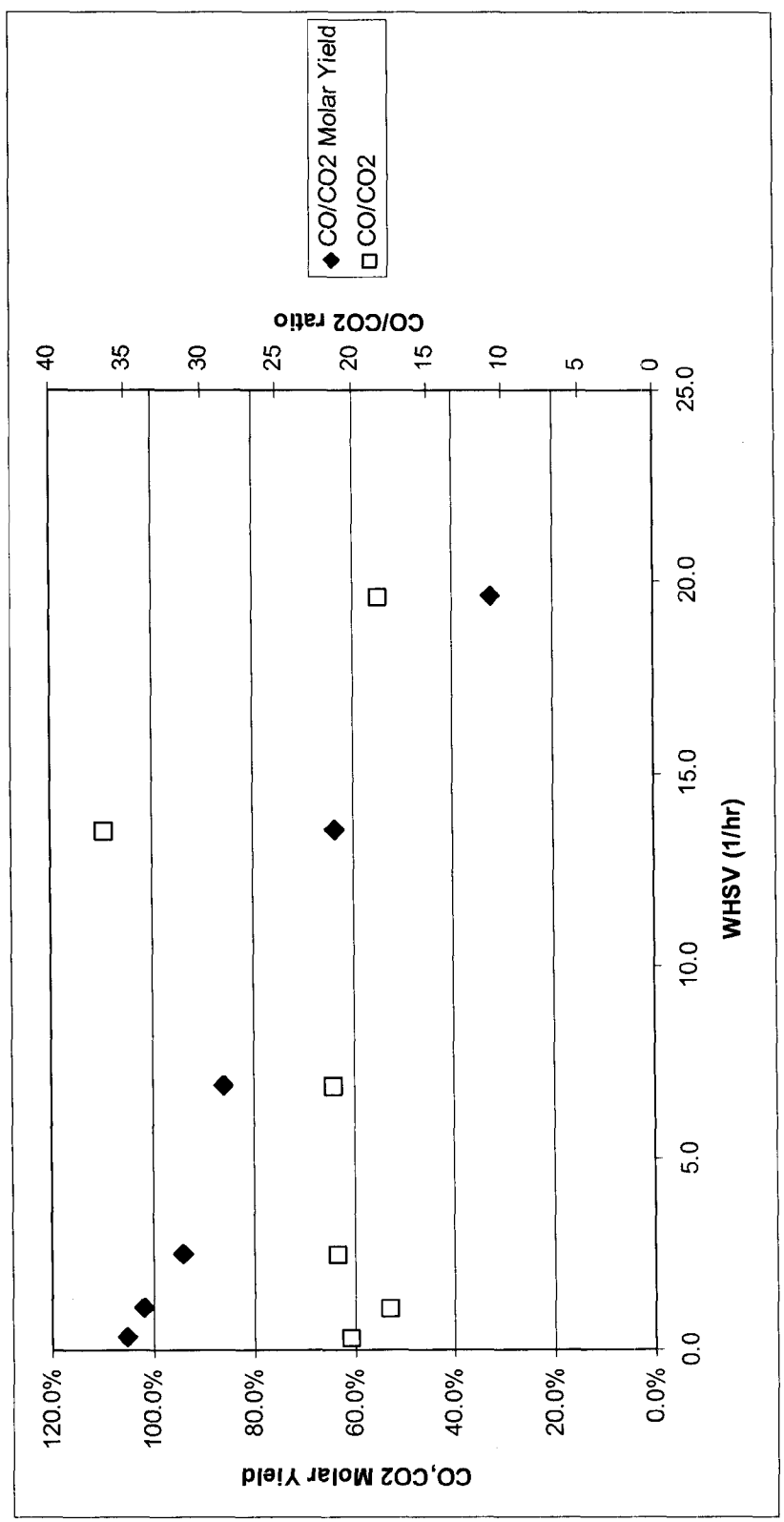
FIG. 1 is a graph depicting molar yields of CO and $CO_2$ at increasing space velocity over amorphous silica-alumina at 773 K and 25 cm$^3$ of gas flow (♦=CO/$CO_2$ molar yield; □=CO/$CO_2$).

The inventors have identified levulinic acid (LA) as a principal, small-molecule product derived from biomass due to its ease of production from both five- and six-carbon sugars.

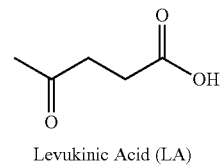

Levukinic Acid (LA)

Its two functional groups (a ketone and a carboxylic acid) make LA an attractive intermediate for producing a host of value-added products. LA is one of the primary degradation products of acid-treated sugars and can be produced from biomass carbohydrates derived from any source, including (but not limited to) municipal waste streams, agricultural waste, lawn clippings, stover, and the like. Producing LA via acid hydrolysis of biomass (e.g., the "Biofine" process) costs approximately $0.40 to 0.50 per pound (in 2009 U.S. dollars).

Very briefly, the "Biofine" process is described in U.S. Pat. No. 5,608,105, issued Mar. 4, 1997, to Stephen W. Fitzpatrick, a copy of which is attached hereto and incorporated herein. (The term "Biofine" as applied to the process was once trademarked in the United States, see Registration No. 1,661,325. However, that registration was cancelled in 1995.)

The process is carried out in a continuous fashion in a two-stage reactor. In the first stage of the reactor, a carbohydrate slurry in water is hydrolyzed in the presence of acid to yield hydroxymethylfurfural and other reaction intermediates. In the second stage of the reactor, the hydroxymethylfurfural and other reaction intermediates are hydrolyzed in the presence of a mineral acid to yield LA. The yield of levulinic acid is quite good, generally over 60% of theoretical. See also "Biorefineries—Industrial Processes and Products," B. Kamm, P. R. Gruber, M. Kamm, Eds.© 2006, Wiley-VCH Verlag GmbH & Co. KGaA, which includes an entire chapter devoted to a discussion of the "Biofine" process.

The "Biofine" process is the starting point for the present method because it is capable of producing a ready and cheap supply of LA derived from renewable biomass sources. The present method uses the LA as a reactant. The LA is converted into a host of value-added chemicals, including acetone, butanone, 4-hydroxy-2-butanone, and methyl vinyl ketone (MVK), a widely utilized alkylating reagent and chemical intermediate.

There are several possible reactive pathways from LA to other reactive chemicals. Reactions involving dehydration (removal of water), hydrogenation (addition of hydrogen), and decarbonylation (removal of carbon) of LA are shown in Scheme 1.

converted into γ-valerolactone (4). In the scientific literature and patents, this process is typically carried out at low temperatures using a metal-based catalyst. These conditions are used to prevent the formation of α-angelica lactone (2) and β-angelica lactone (3), an endothermic and acid-catalyzed process. These lactones (2 and 3) are known to poison metal-containing catalysts by forming solid carbon residues or tar on the surface of the catalysts. The carbon residue inhibits the reactive sites on the surface of the catalysts. By operating at low temperatures over a metal catalyst, LA is first hydrogenated to form 4-hydroxy pentanoic acid (5). Compound 5 readily dehydrates to yield γ-valerolactone (4). Much attention in the literature and patents has thus focused on the hydrogenation and subsequent dehydration of 4 to yield 2-methyltetrahydrofuran (6), a solvent and oxygenated gasoline additive.

The present method diverges from all previous work by focusing on producing chemicals from LA without adding hydrogen. From a financial point of view, this approach enables the use of less-costly catalysts and reaction conditions. Reactions involving hydrogen typically require precious metal catalysts such as Pt, Pd, Ru, Ir, Ni, and the like. Additionally, hydrogenation reactions require a source of relatively pure hydrogen. These hindrances, however, are eliminated by using a method that does not require molecular Scheme 1.
Possible Reaction Pathways of Levulinic Acid:
Dehydration, Hydrogenation and Decarbonylation

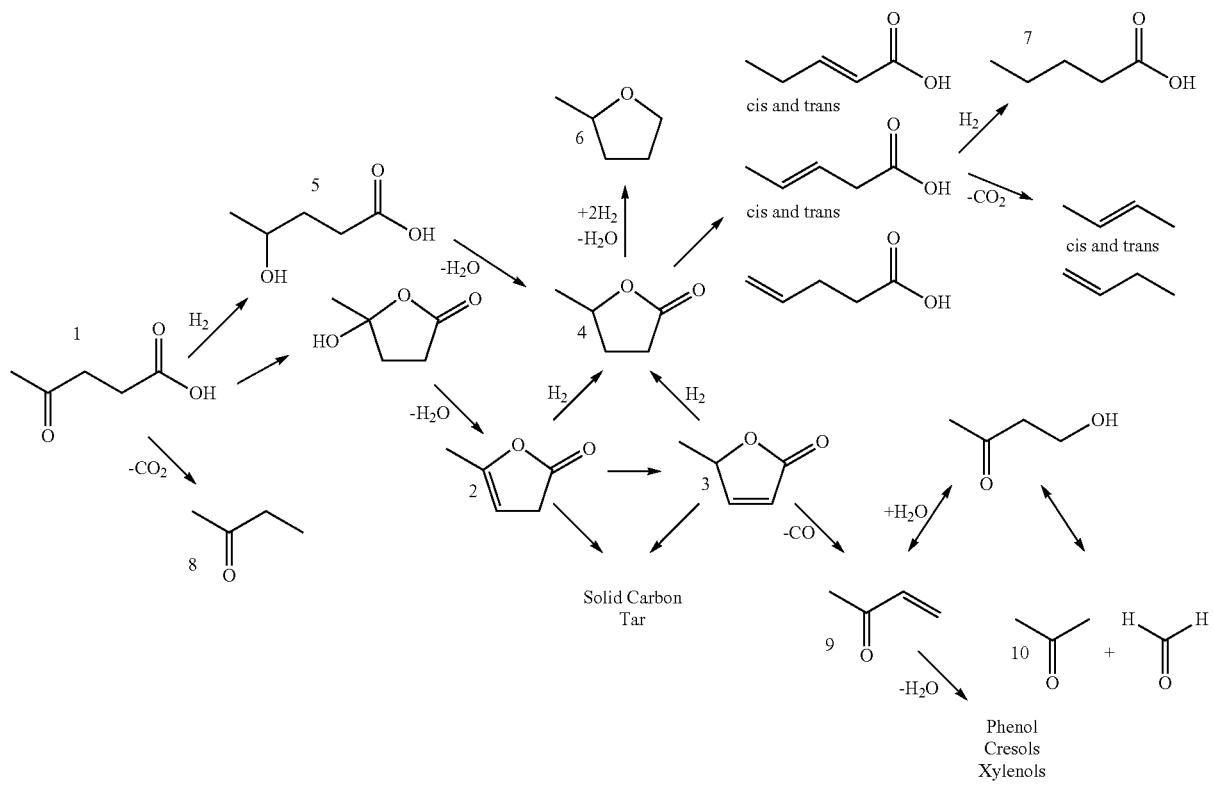

In Scheme 1, LA is compound 1 and MVK is compound 9. Thus, the present application will focus largely on the reactions shown in the lower portion of Scheme 1. Previous work by the present inventors has focused on dehydration and hydrogenation reactions of LA. Thus, in prior work, LA (1) is hydrogen ($H_2$) as a reactant. Thus, the present method can be carried out in the absence of molecular hydrogen, and without adding molecular hydrogen as a reactant.

One such hydrogen-neutral process encompassed by the present method is the production of butanone (8). In initial studies, butanone and carbon dioxide were found to be by-products resulting from a minor side reaction. Attempts were then made to maximize the minor side reaction to make it the principal pathway. This led to a serendipitous discovery. As previously mentioned, in conventional reactions of levulinic acid, the production of angelica lactones (2 and 3) is minimized to the greatest extent possible because the lactones are known to foul catalysts due to the formation of tar and carbon deposits. Angelica lactones are typically formed over solid acid catalysts at moderate temperatures (about 420 to 620 K) where their production is a hydrogen-neutral reaction.

The present inventors discovered that by reacting LA at high temperatures over solid acid catalysts, MVK (9) could be produced in high yields. While not being limited to any underlying mechanism or mode of action, it is believed that this reaction could involve both a direct reaction of LA (1), and also a reaction of the angelica lactones 2 and 3. Production of MVK using the present method also co-produces carbon monoxide, CO. By monitoring the amount of CO produced, it is estimated that from about 90% to about 97% of the LA can be reacted to form MVK with the remaining 10% to 3% going to form butanone (8) and $CO_2$. The production of MVK from LA is both novel and unobvious.

Again, while not being limited to any particular mechanism, possible chemical routes of this conversion are shown specifically in Scheme 2. It is important to note that these routes do not require molecular hydrogen as a reagent because they are acid-catalyzed processes (as denoted with $H^+$).

a hindrance in producing MVK from biomass due to its tendency to react further with other chemical entities in the reaction solution.

Theoretical studies of the reaction shown in Scheme 2 show that MVK can be produced in high yields (90+%) provided the reaction conditions are optimized to reduce further reactions of MVK. In experiments testing Scheme 2, the yield of CO produced was very high, indicating that the majority of the LA is proceeding through this route and making MVK. FIG. 1, for example, is a graph showing the CO and $CO_2$ yield (moles of species/moles of inlet LA) and $CO:CO_2$ ratio as a function of inlet flow. Specifically, FIG. 1 depicts the molar yields of CO and $CO_2$ at increasing space velocities. The reaction was conducted over amorphous silica-alumina at 773 K and 25 $cm^3$ of gas flow. No other chemical species were observed (beyond MVK) that could account for the level of CO produced. At low space velocities, the molar yield of CO and $CO_2$ was near 100% of the inlet flow of LA, indicating near complete conversion to MVK and 2-butanone. (See Scheme 1: the production of CO corresponds to the production of MVK (9); the production of $CO_2$ corresponds to the production of 2-butanone (8).)

At low space velocities, however, MVK can degrade by several mechanisms. The MVK can further react to yield acetone (through the reverse reaction of the current industrial process to make MVK). The MVK can also condense with itself to yield phenols, cresols, and xylenols. See Scheme 1, lower right.

Scheme 2.
Possible Chemical Routes in the Production of
Methyl Vinyl Ketone (MVK) from Levulinic Acid (LA)

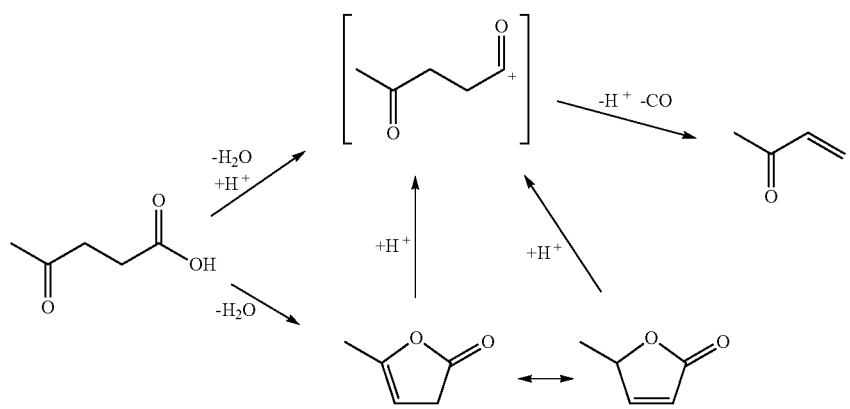

Figure 2:
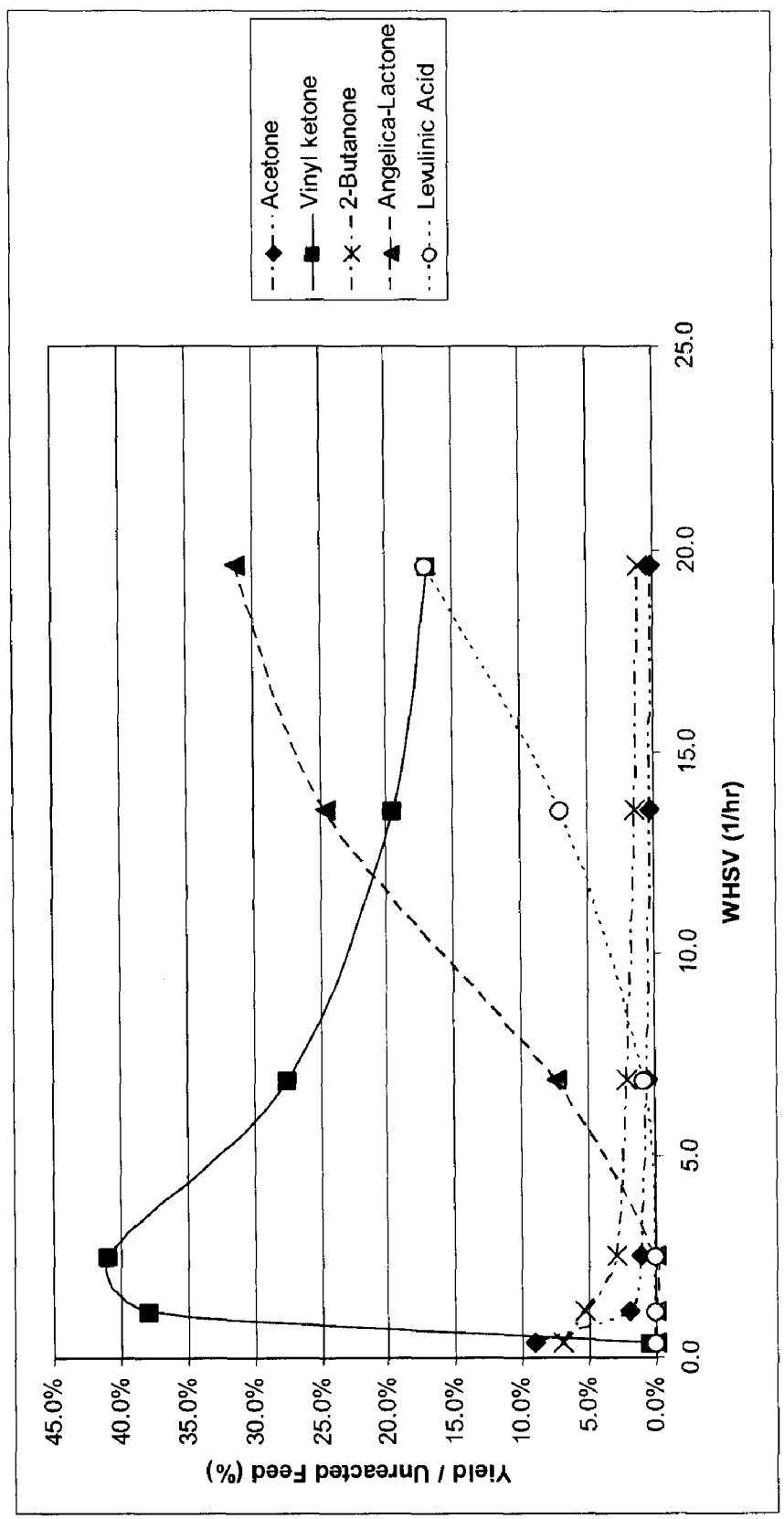
FIG. 2 is a graph depicting the yield (wt %) of various products (or unreacted levulinic acid) at increasing space velocity over amorphous silica-alumina at 773 K and 25 cm$^3$ of gas flow (♦=acetone, ■=vinyl ketone; x=2-butan one; ▲=angelica lactone; o=levulinic acid).

MVK contains two functional groups, namely a ketone and an olefin. These functional groups make MVK reactive and valuable for a number of industrial processes. The current route to producing MVK is included in Scheme 1, namely acetone (10) and formaldehyde are reacted to form 4-hydroxy-2-butanone which is then dehydrated to form MVK (9). MVK is a good alkylating agent because the olefin group makes is an effective acceptor in alkylation reactions. That is, MVK is a good Michael acceptor. MVK is used in the production of plastic polymers and also many other practical chemical pathways. For example, it is used as a reagent in the synthesis of Vitamin A. On one hand, the reactive nature of MVK makes it a very promising chemical to produce from biomass. On the other hand, that same reactive nature is also FIG. 2 is a graph depicting the results of a preliminary study on the production of MVK from LA as a function of space velocity. (In FIG. 2, the flow rate of levulinic acid was normalized by the mass of catalyst.) Thus, FIG. 2 is a graph depicting the yield of various products (or unreacted LA) at increasing space velocity over amorphous silica-alumina at 773 K and 25 $cm^3$/min of gas flow. This study was conducted in an up-flow reactor. It is important to note that the catalyst, while a strong acid catalyst, does not contain a defined structure (unlike a zeolite) and is one of the least costly and most abundant types of acid catalysts available. It is likely that other acid catalysts will display much higher activity. All acid catalysts, now known or developed in the future, can be used in the method.

Yields of approximately 45% to 90% MVK were observed at space velocities of from about 1 to 2 $hr^{-1}$ in the initial study.

Optimization of the reactive conditions, including catalysts, temperatures, and pressures could result in higher yields.

The overall chemistry for the production of MVK from a six-carbon sugar is shown in Scheme 3. In the formation of LA from sugar, formic acid is produced, while in the reaction of LA to MVK, carbon monoxide is produced (Scheme 3A). Formic acid and carbon monoxide can be reformed to $H_2$ and $CO_2$, as shown in Scheme 3B, such that hydrogen could be a potential byproduct of the present method. In addition, this hydrogen could be reacted to form 2-butanone by hydrogenating the C—C double bond of MVK as shown in Scheme 3C. This approach yields a biomass-derived source of 2-butanone, another commodity chemical.

Scheme 3:
Overall Balance of Sugar to MVK and other Direct Products (A), Sugar to MVK and Reformed Products (B), and Sugar to 2-Butanone and Other Reformed Products (C)

A.

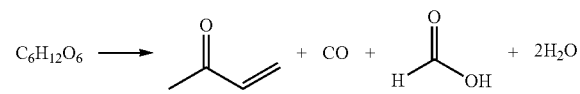

B.

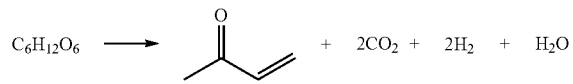

C.

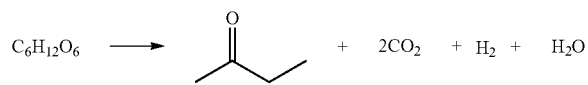

The low cost of levulinic acid and acid catalyst makes the present method an economical way of producing a highly reactive, and useful compound from biomass without having to supply molecular hydrogen to the reaction.

EXAMPLES

The following examples are included solely to provide a more thorough description of the method disclosed and claimed herein. The examples do not limit the scope of the method in any fashion.

Experimental

Amorphous silica-alumina (MCC 25, Grace Davidson with a Si/Al ratio of 4), niobic acid (HY-340, Companhia Brasileira de Metalurgia e Mineração (CBMM)), USY-zeolite (Si/Al=5, Engelhard), and sulfated zirconia (MEI Chemicals) were used as received.

Experiments were carried out in an ¼" outside diameter stainless steel tubular upflow reactor loaded with 0.1-2 grams of acid catalyst mixed with crushed quartz chips (to reduce reactor dead volume) and held in place by quartz wool (Altech).

In a typical experiment, the catalysts were heated to the desired temperature under flowing hydrogen. The hydrogen flow was then discontinued and liquid flow was then started. The feed for all runs comprised 10 wt % levulinic acid solution in water.

Insulated aluminum blocks were heated using a K-type thermocouple (Digi-Sense) between the blocks and reactors to monitor the temperature, which was controlled by a series 16A temperature controller (Love Controls). The He flow rate was controlled with a 5850E Brooks Instruments mass flow controller while the liquid feed was controlled with a Lab Alliance Series 1 HPLC pump. The liquid effluents were drained from the separator and analyzed by GC (Shimadzu GC-2010, FID, SHRX5 column) and by GC-MS (Shimadzu GC-2010 SHRX1-5MS column). Gas effluents were analyzed by a He sweep through the separator which then passed through a Carle GC (Series 400 AGC, TCD, Porapak Q column) for CO, $CO_2$ and a Varian GC (Saturn 3, FID, GS-Q column (J&W Scientific)) for gaseous hydrocarbons. Typical total material balances closed to 100±10%.

Results

The first group of reactions to consider from levulinic acid proceeds without the addition of hydrogen; they are dehydration and decarbonylation. The dehydration of levulinic acid is shown in Scheme 4, and likely proceeds through the pseudo-levulinic acid intermediate. This intermediate is predicted based on UV adsorption patterns, observed cyclic esters and acylated enols, see [1] and the references cited therein. Dehydration of this pseudo-levulinic acid leads to α-angelica lactone which can then isomerize to β-angelica lactone. The β-angelica lactone is expected to be slightly more stable as the C—C double bond is conjugated with the C—O double bond.

Scheme 4.
Dehydration and Isomerization of
Levulinic acid in the Angelica-Lactones.

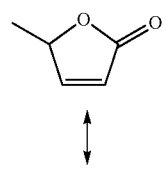

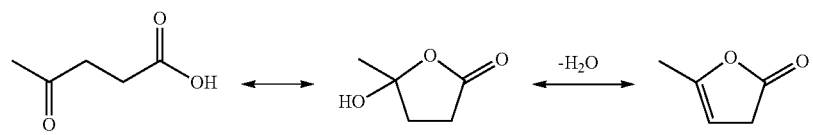

The interconversion between these species is easily accomplished due to low barriers. The predicted change in Gibbs energy and enthalpy between levulinic acid and α-angelica lactone is around 10 and 78 kJ/mol respectively, while between α-angelica lactone and β-angelica lactone it is 5 and 3 kJ/mol, respectively with the α-angelica lactone predicted to be slightly more stable than the β-angelica lactone (i.e., $\Delta G^{\alpha-\beta}$=−5 kJ/mol, β-lactone to α-lactone). The production of α-angelica lactone from levulinic acid can be accomplished at low temperatures under vacuum distillation condition [2]. The reactive distillation takes advantage of the lower vapor pressure of α-angelica lactone relative to levulinic acid to remove this product and prevent the back reaction from occurring. At the same time, the low temperature limits the isomerization to β-angelica lactone. Further literature evidence for this back reaction can be found in the production of levulinic acid esters from angelica lactones [3,4] or levulinic acid from angelica lactones [1]. Starting from the angelica lactones, under acidic conditions, the esters of levulinic acid can be produced by ring opening in which the alcohol tail attaches to the carboxylic acid [3,4]. Alternatively, under acidic aqueous conditions, the angelica lactones can be rehydrated to reform levulinic acid, [1].

The gas phase equilibration between these species was studied over amorphous silica alumina and niobic acid. In these studies, a 10 wt % aqueous solution of levulinic acid was swept through a heated catalytic bed by an inert gas stream and collected in a separator at atmospheric pressure. To ensure the system was attaining equilibrium, a feed solution of 5 wt % α-angelica lactone was also tested. It was found that the system quickly equilibrates with the relative ratio of α-angelica to β-angelica lactone shown in FIG. 3 for several representative experiments. From even a cursory glance at FIG. 3, it is apparent that the relative distribution does not change strongly with temperature. Assuming the system is at equilibrium, equation 1 can be written. This equation can then be solved for the thermodynamic variables ΔH and ΔS as shown in equation 2.

$$\frac{P_\alpha}{P_\beta} = K_{eq}^{\alpha-\beta} = \exp\left(\frac{-\Delta G^{\alpha-\beta}}{RT}\right) = \exp\left(\frac{-\Delta H^{\alpha-\beta}}{RT} + \frac{\Delta S^{\alpha-\beta}}{R}\right) \quad (1)$$

$$-RT \ln\left(\frac{P_\alpha}{P_\beta}\right) = \Delta H^{\alpha-\beta} - \Delta S^{\alpha-\beta} T \quad (2)$$

Because the isomerization between lactones does not involve a change in the number of moles, and because the lactones are so similar in chemical structure, the change in entropy, ΔS, is expected to be quite small, such that the equation 2 is expected to show very little or no temperature dependence. Plotting equation 2 in FIG. 4 reveals that, as expected, little to no temperature dependence is found, with $\Delta G^{\alpha-\beta}=\Delta H^{\alpha-\beta}$=1.4±0.4 kJ/mol (β-lactone to α-lactone). Hence the β-angelica lactone (as expected) is slightly more stable than α-angelica lactone with only a 1.4 kJ difference between them.

The isomerization of angelica lactones, however, is known to occur on very weak sites, even within a GC column/injector port. One study found that all three isomers of angelica lactone (α,β and γ) can be detected from isomerization during the course of a GC run where the history of the column (temperature, form, insert acidity) influences the isomerization [5]. After passing through a typical column, the ratio of α/β is approximately 17 indicating that the species are not reaching equilibrium, but also showing the ease of isomerization within a relatively inert environment. After injecting diethyl amine to neutralize acidic sites, the ratio increased to approximately 160, indicating that weakly acidic sites can easily isomerize the lactones [5].

With the thermodynamics of the lactones established, the thermodynamics of the dehydration/rehydration shown in Scheme 4 could be examined. This step is slightly more complicated as it directly involves three chemicals, levulinic acid, water and α-angelica lactone, and indirectly β-angelica lactone through rapidly equilibrated isomerization. At equilibrium, the equilibrium constant can be written as shown in equation 3 and solved to yield equation 4. Equation 4 is plotted for several sets of experiments versus temperature in FIG. 5.

$$K_{eq}^{lev-lac} = \frac{P_{H_2O} P_{\alpha-lactone}}{P_{levulinic\_acid}} = \frac{y_{H_2O} y_{\alpha-lactone} P_{total}}{y_{levulinic\_acid}} = \quad (3)$$

$$\exp\left(\frac{-\Delta G^{lev-lac}}{RT}\right) = \exp\left(\frac{-\Delta H^{lev-lac}}{RT} + \frac{\Delta S^{lev-lac}}{R}\right)$$

$$-RT \ln\left[\frac{y_{H_2O} y_{\alpha-lactone} P_{total}}{y_{levulinic\_acid}}\right] = \Delta H^{lev-lac} - T\Delta S^{lev-lac} \quad (4)$$

Figure 5:
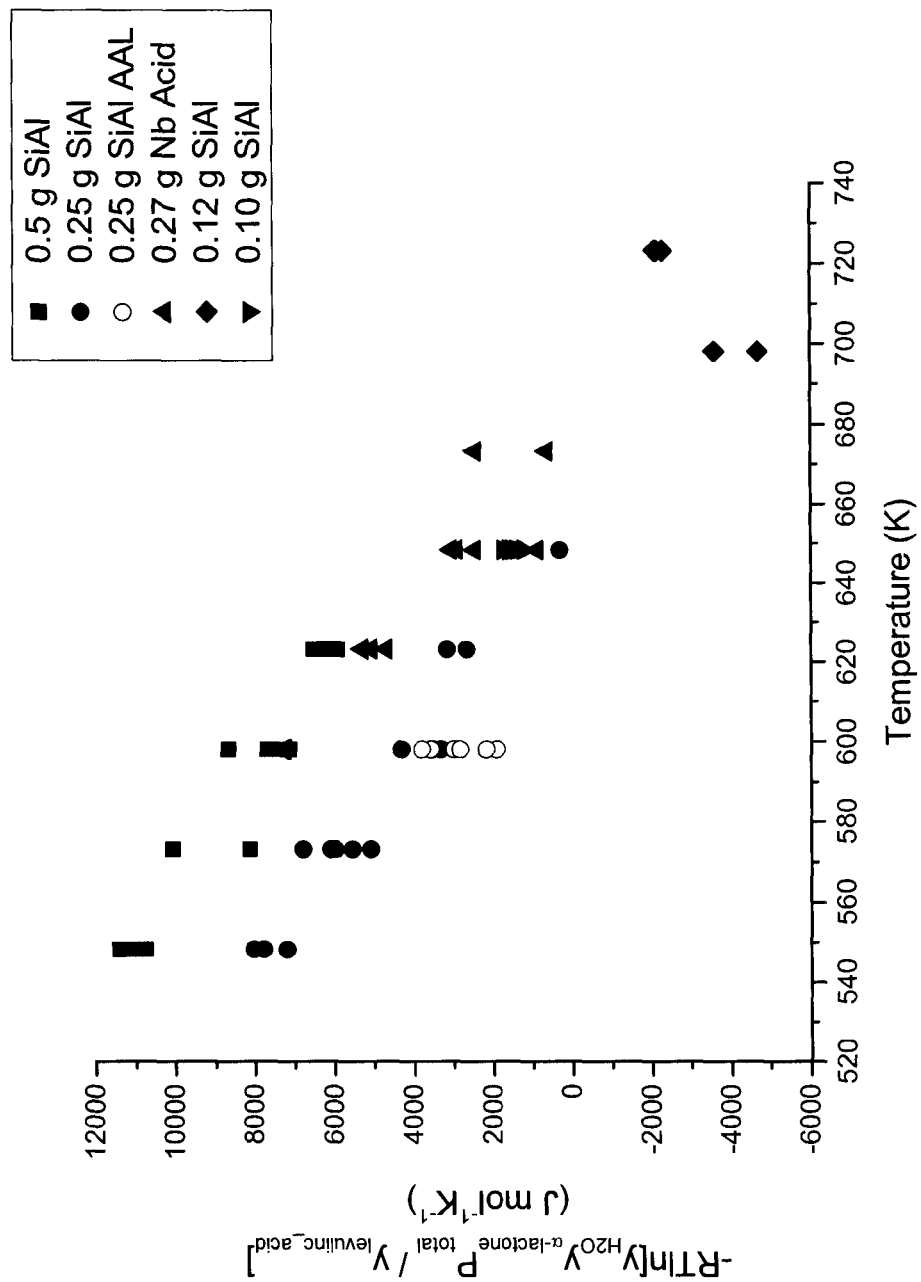
FIG. 5 is a graph depicting the inter-conversion of levulinic acid, water, and α-angelica lactone. The Y-axis depicts the -RT ln ($y_{H2O}y_{\alpha\text{-}angelica\ lactone}P_{total}/y_{levulinic\ acid}$). (■=0.5 g SiAl; ●=0.25 g SiAl; o=0.25 g SiAl α-angelica lactone (AAL) feed; ▲=0.27 g Nb acid; ♦=0.12 g SiAl; ▼=0.10 g SiAl).—

The experiments shown in FIG. 5 were conducted with varied amounts of catalyst as shown in the legend. Included in FIG. 5 are data from a 5 wt % α-angelica lactone feed (and 0.25 g of catalyst) with similar results. "AAL" designates α-angelica lactone. The average thermodynamic values extracted from FIG. 5 using equation 4 are an enthalpy change of 48±6 kJ/mol and an entropy change of 72±9 J/mol.

Figure 6:
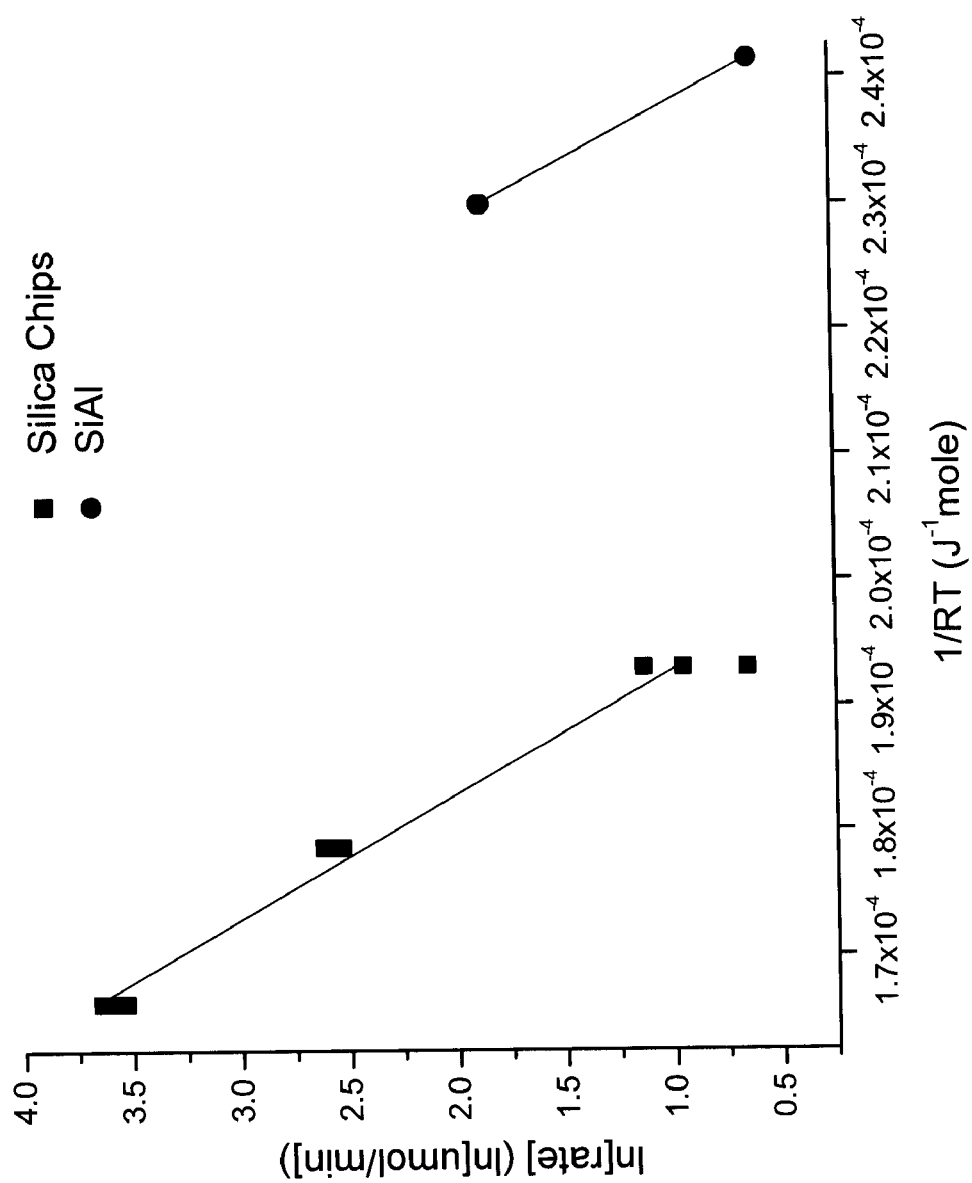
FIG. 6 is a graph depicting the rate of production of angelica lactones from a 10 wt % levulinic acid solution in water over crushed silica chips and silica alumina (■=silica chips; ●=SiAl).

The assumption that the acid sites were enabling the rapid equilibration was also investigated. The system was run under identical conditions in the absence of acid catalyst using a bed of crushed silica. A plot of the rate of production (μmol/min) versus reciprocal temperature is shown in FIG. 6 for the temperature range of 623-723 K. From this experiment, the predicted activation energy for the dehydration over silica chips is 101 kJ/mol. For comparison, the rate of production (μmol/min) is given for low temperatures (498-523 K) using 0.5 g of silica alumina mixed with crushed silica chips. In the presence of solid acid, the rate of production of lactones at 498 K is similar to the rate of production without catalysts at 623 K. For both of these runs, the α and β isomers of angelica lactone were detected in the effluent. However, the ratio of α/β was much greater than 1 for all data points, indicating that these species were not inter-equilibrated.

Decarbonylation Using Solid Acid Catalysts

From an overall perspective, the simplest products one could produce from levulinic acid are methyl vinyl ketone (MVK) and 2-butanone (methyl ethyl ketone). The production of these species requires only the direct reaction of levulinic acid, or direct reaction the dehydration product, α-angelica lactone as shown in Scheme 5. The decarboxylation of levulinic acid to produce 2-butanone releases $CO_2$, making it a highly favored reaction. Conversely the dehydration to produce α-angelica lactone can be followed with the highly endothermic decarbonylation to produce MVK and release CO. The CO released can react with the water in this later reaction via the water gas shift reaction to produce $H_2$. The hydrogen so produced could be used in a subsequent step to hydrogenate the MVK back to 2-butanone (a highly exothermic process, $\Delta H_r°$=−123.7 kJ/mol[6]).

Scheme 5.
Production of Methyl Vinyl Ketone (MVK) and
2-Butanone from Levulinic Acid (LA).

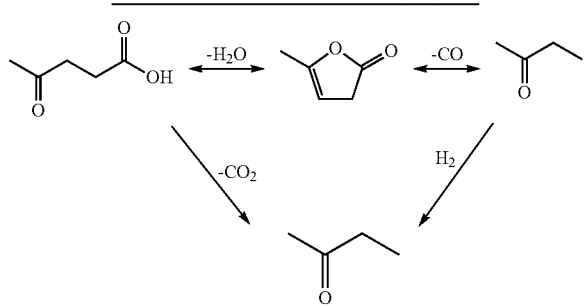

The direct decarboxylation of LA to yield 2-butanone has been attempted in a few cases [7,8]. An attempt at decarboxylation in hydrogen, at standard pressure, 603 K, over a Pd-supported catalyst, yielded no 2-butanone, despite high activity for other substituted carboxylic acids[7]. Over a Cu faujasite catalyst, 54% conversion of levulinic acid was noted at 491 K. However the yield to 2-butanone was not given [8]. The difficulty in performing this reaction is not surprising however. The dehydration of levulinic acid proceeds quite readily to form the angelica lactones even in a bed of relatively unreactive silica. The lactones are known precursors to coke and tar, and have been noted to block acidic and metallic sites [9,10]. Therefore at elevated temperatures, this reaction is possible, but the competing and more thermodynamically favored dehydration makes it difficult to occur.

The decarbonylation of levulinic acid and α-angelica lactones to form MVK has been noted [11-14]. In the photochemical decarbonylation of α-angelica lactone and other similar species, it is noted that a C—C double bond adjacent to the ether oxygen is required for clean cleavage [12]. A similar conclusion was reached on a study of gaseous α-angelica lactone and related species through a quartz tube [14]. The onset temperature of decarbonylation of α-angelica lactone through quartz tubes has been reported as 748 K [13] to 793 K [14] with an 74% yield of MVK at 843 K over silica chips [11].

The enthalpy change to form MVK from α-angelica lactone is very endothermic. Therefore the high temperatures noted for this reaction are expected. Interestingly enough, it has been reported that the reverse reaction, namely the carbonylation of MVK to levulinic acid in water can be accomplished at low temperatures namely, 373-383 K using a Pd-catalyzed system in excess HCl and under a 50-150 bar CO pressure [15]. The authors note that the yield increases with increasing CO pressure and that the yield passes through a low temperature maximum at around 383 K and falls off at increasing temperature. Therefore the forward endothermic reaction to form MVK can be accomplished at high temperatures in the gas phase over silica, while the reverse reaction can be induced through excess CO and low temperatures.

Results of MVK Production

Figure 7:
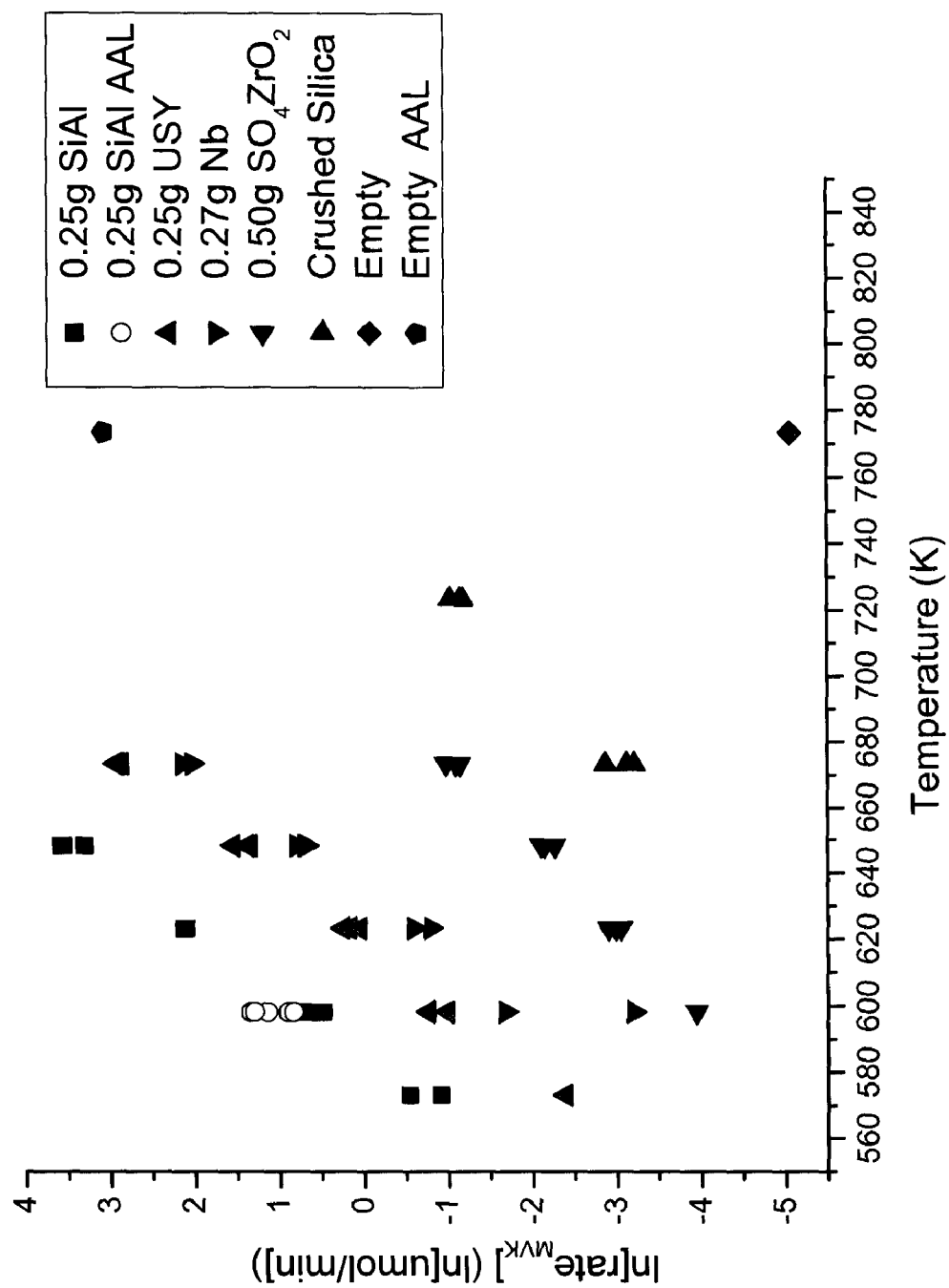
FIG. 7 is a graph depicting the rate of production of methyl-vinyl ketone vs. temperature through an equal total volume of reactor (■=0.25 g SiAl; o=0.25 g SiAl AAL; Δ=0.25 g USY; ▼=0.27 g Nb; ◄=0.50 g $SO_4ZrO_2$; ▶=crushed silica; ♦=empty reactor, LA feed; pentagon=empty reactor, AAL feed). "AAL"=α-angelica lactone.

Previous results have shown that MVK can be produced either over a bed of silica or in a quartz reactor tube. In these systems, the onset temperature of decarbonylation of α-angelica lactone ranges from 748 K [13] to 793 K [14] with an 74% yield of MVK at 843 K over silica chips [11]. FIG. 7 shows the production of MVK from either a 10 wt % levulinic acid or 5 wt % α-angelica lactone in water feed solution as a function of temperature. Two blank runs in an empty stainless steel reactor tube were performed as a reference for the two feed solutions. Next, the bed was packed with only silica chips, to repeat previous results and to establish the effect of the silica chips on the reaction. Lastly, 0.25-0.5 grams of acid catalyst was mixed with silica chips and loaded into the reactor. In this way, the amount of silica chips in the reactor remained constant for all runs involving an acidic catalyst. The rate is given as the natural log of μmoles of MVK produced per minute through the reactor.

From FIG. 7, it is apparent that even when reacted in an empty reactor, α-angelic lactone is able to react to MVK relatively easily at 773 K. See the pentagon in the upper-right corner of the graph shown in FIG. 7. In contrast, levulinic acid is unable to do so in the same reactor. See the diamond in the lower-right corner of the graph shown in FIG. 7. Filling the reactor with silica chips greatly increases the rate of MVK production. This production is accompanied by the observed production of both isomers of angelic lactone. Adding $SO_4ZrO_2$ increased the rate slightly more, while Nb, USY and SiAl addition greatly increased the rate of MVK production, with SiAl increasing the most. With SiAl, as noted in FIG. 5, the rate of isomerization between levulinic acid, and the angelic lactone isomers occurred rapidly at 673 K such that an equilibrium mixture of these species is quickly reached in the reactor. Thus, the rate of production of MVK from either a levulinic acid feed or α-angelic lactone feed was very similar for SiAl under these near-equilibration conditions.

As noted above, the α-angelic lactone is believed to be the intermediate in the production of MVK from levulinic acid. Accordingly, the rate of production of MVK over solid acid catalysts should depend upon the partial pressure of α-angelic lactone within the reactor as shown in equation 5.

$$r_{MVK} = k_{MVK} P_{\alpha\text{-lactone}} \quad [5]$$

Figure 3:
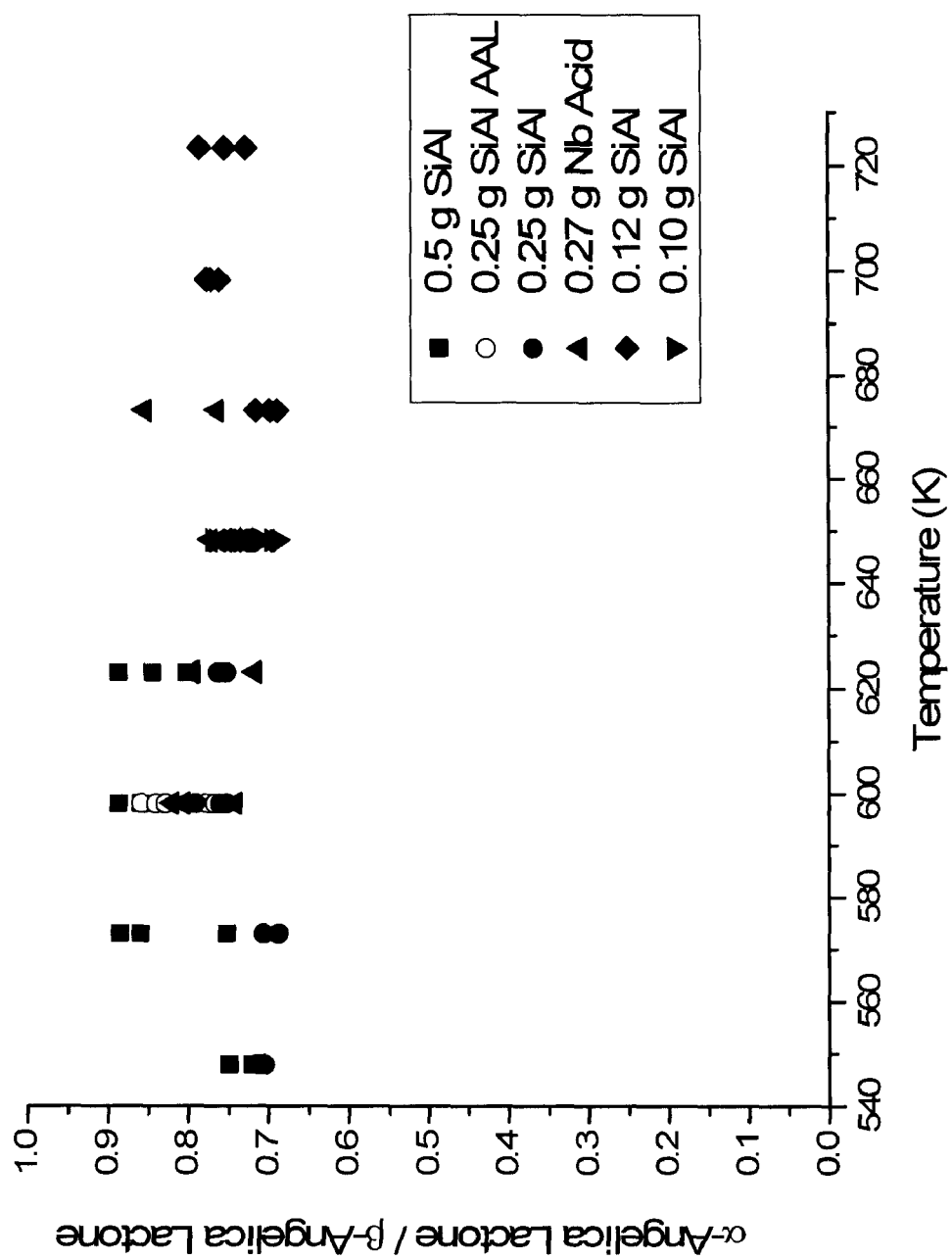
FIG. 3 is a graph depicting the isomerization of α-angelica lactone to β-angelica lactone as a function of temperature for a levulinc acid feed. The Y-axis depicts the ratio of α-angelica lactone to β-angelica lactone (■=0.5 g SiAl; o=0.25 g SiAl α-angelica lactone (AAL) feed; ●=0.25 g SiAl; ▲=0.27 g Nb acid; ♦=0.12 g SiAl; ▼=0.10 g SiAl).
Figure 4:
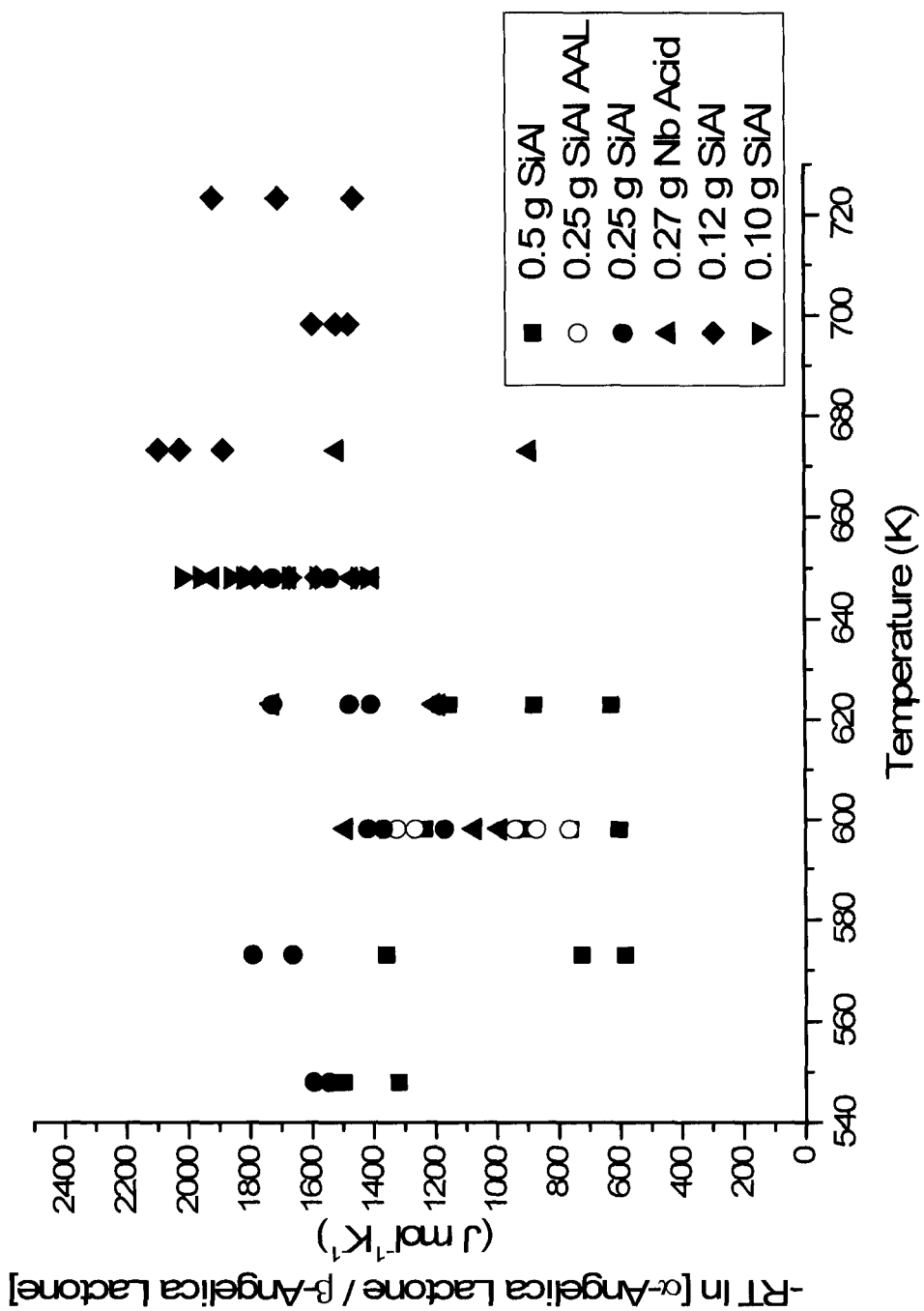
FIG. 4 is a graph depicting the isomerization of α-angelica lactone to β-angelica lactone as a function of temperature for a levulinic acid feed. The Y-axis depicts the -RT ln (α-angelica lactone/β-angelica lactone) (■=0.5 g SiAl; o=0.25 g SiAl α-angelica lactone (AAL) feed; ●=0.25 g SiAl; ▲=0.27 g Nb acid; ♦=0.12 g SiAl; ▼=0.10 g SiAl).
Figure 8:
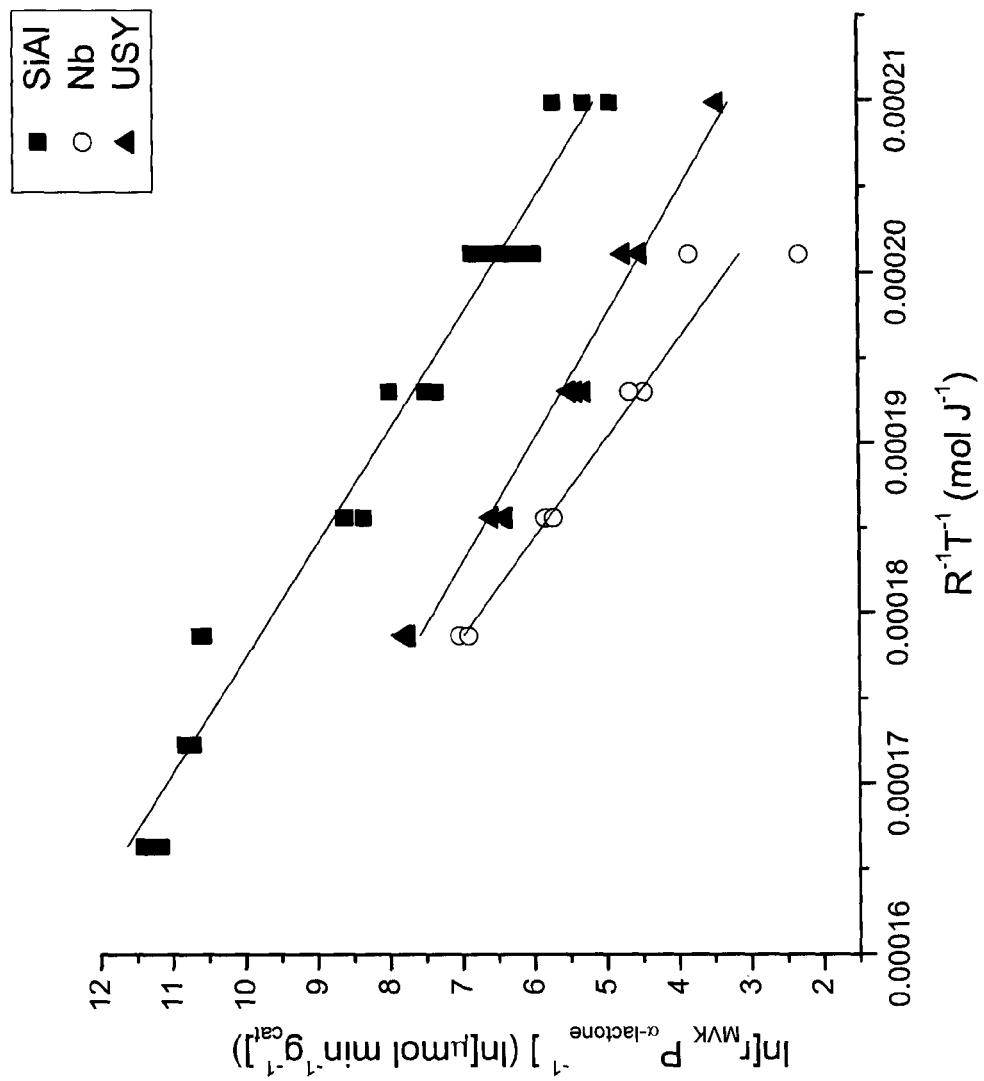
FIG. 8 is a graph depicting the production of methyl-vinyl ketone normalized by partial pressure of α-angelica lactone (■=SiAl; o=Nb; ▲=USY).

As shown in FIGS. 3, 4, and 5, the interconversion between the lactones, water and levulinic acid occurs rapidly when a solid acid catalyst is present. As a first approximation for solving equation 5, the equilibrium partial pressure of α-angelica lactone can be calculated for each set of reacting conditions by solving the thermodynamics in equations 1-4 concurrently with the material balances. The rate of MVK production can then be represented as the observed rate divided by the calculated partial pressure of α-angelica lactone. As derived in equation 6 and shown in FIG. 8, the simple Arrhenius parameters for the forward rate constant can be calculated by plotting the natural logarithm of the observed rate divided by the α-angelica lactone pressure versus 1/RT. The data in FIG. 8 for SiAl incorporates the various runs of different catalysts loadings that attained equilibrium shown in FIG. 5.

$$\ln[k_{MVK}] = \ln[r_{MVK} P^{-1}_{\alpha\text{-lactone}}] = \ln[A_{MVK}] - \frac{Ea_{MVK}}{RT} \quad [6]$$

From FIG. 7 and equation 6, the kinetic parameters for the catalysts are shown in Table 1, along with the measured surface acid site concentration. It is apparent that SiAl is the most active catalyst on a per mass basis, followed by USY and lastly by Nb. On a per acid site basis, SiAl was still the most active catalyst tested, followed by Nb and lastly USY.

TABLE 1

Arrhenius Parameters from FIG. 7 and Equation 6.

| | Surface Acid Concentration ($\mu mol\ g_{cat}^{-1}$) | Ea (kJ mol$^{-1}$) | ln[A] (ln[$\mu mol\ min^{-1}\ g_{cat}^{-1}\ bar^{--1}$]) |
|---|---|---|---|
| SiAl | 578 | 149 | 36 |
| USY | 1015 | 137 | 32 |
| Nb | 135 | 171 | 38 |

REFERENCES

[1] R. H. Leonard, J. Ind. Eng. Chem. (Washington, D.C.) FIELD Full Journal Title: Journal of Industrial and Engineering Chemistry (Washington, D.C.), 48 (1956) 1331.

[2] R. H. Leonard, Conversion of levulinic acid into alpha-angelica lactone. (Heyden Newport Chemical Corp.). US, 1957.

[3] L. E. Manzer, Preparation of levulinic acid esters from alpha-angelica lactone and alcohols. (E.I. Dupont de Nemours and Company, USA). Application: WO WO, 2005, p. 24 pp.

[4] L. E. Manzer, Catalytic preparation of levulinic acid esters from alpha-angelica lactone and alcohols for use as fuel octane-boosting additives. (E.I. Du Pont De Nemours and Company, USA). Application: US US, 2005, p. 12 pp.

[5] M. Zviely, R. Giger, E. Abushkara, A. Kern, H. Sommer, H.-J. Bertram, G. E. Krammer, C. O. Schmidt, W. Stumpe and P. Werkhoff, Spec. Publ.—R. Soc. Chem. FIELD Full Journal Title: Special Publication—Royal Society of Chemistry, 277 (2002) 39.

[6] NIST Chemistry WebBook (NIST Standard Reference Database Number 69). U.S. Secretary of Commerce 2009.

[7] W. F. Maier, W. Roth, I. Thies and P. v. R. Schleyer, Chem. Ber. FIELD Full Journal Title: Chemische Berichte, 115 (1982) 808.

[8] L. A. Pine, Decarboxylation of carboxylic acids. (Esso Research and Engineering Co.). Application: US US, 1969, p. 3 pp.

[9] P. M. Ayoub and J.-P. Lange, Process for converting levulinic acid into pentanoic acid. (Shell Internationale Research Maatschappij B.V., Neth.). Application: WO WO, 2008, p. 29 pp.

[10] J.-P. Lange, Process for converting levulinic acid into pentanoic acid. (Shell Internationale Research Maatschappij B. V., Neth.). Application: WO WO, 2009, p. 21 pp.

[11] J. G. M. Bremner and D. G. Jones, Methylvinyl ketone. (Imperial Chemical Industries Ltd.). GB, 1948.

[12] O. L. Chapman and C. L. McIntosh, J. Chem. Soc. D. FIELD Full Journal Title: Journal of the Chemical Society [Section] D: Chemical Communications (1971) 383.

[13] W. Skorianetz and G. Ohloff, Helv. Chim. Acta FIELD Full Journal Title: Helvetica Chimica Acta, 58 (1975) 1272.

[14] Z. P. Xu, C. Y. Mok, W. S. Chin, H. H. Huang, S. Li and W. Huang, J. Chem. Soc., Perkin Trans. 2 FIELD Full Journal Title: Journal of the Chemical Society, Perkin Transactions 2: Physical Organic Chemistry (1999) 725.

[15] G. Cavinato and L. Toniolo, J. Mol. Catal. FIELD Full Journal Title: Journal of Molecular Catalysis, 58 (1990) 251.

What is claimed is:

1. A method for converting levulinic acid to methyl vinyl ketone, the method comprising:
reacting a solution comprising levulinic acid, over an acid catalyst, at a temperature of from room temperature to about 600 K, whereby methyl vinyl ketone is formed.

2. The method of claim 1, comprising reacting the levulinic acid solution over a solid acid catalyst.

3. The method of claim 2, comprising reacting the levulinic acid solution over a solid acid catalyst selected from the group consisting of ceramic acid catalysts, acidic molecular sieves, aluminosilicates, titanosilicates, borosilicates, mixed metallic oxides, phosphated metal oxides, sulfated metal oxides, acidic ion exchange resins, heteropoly acids, and combinations thereof.

4. The method of claim 2, comprising reacting the levulinic acid solution over a solid acid catalyst selected from the group consisting of aluminosilicates, titanosilicates, borosilicates, acidic zeolites, tungstated zirconia, and acidic polyoxymetalates.

5. The method of any one of claims 1-4, comprising reacting the levulinic acid in an aqueous solution, and in the absence of added molecular hydrogen.

6. The method of any one of claims 1-4, comprising reacting the levulinic acid solution at a temperature of from about 300 K to about 600 K.

7. The method of any one of claims 1-4, comprising reacting the levulinic acid solution at a temperature of from about 350 K to about 600 K.

8. The method of any one of claims 1-4, comprising reacting the levulinic acid solution at a temperature of from about 400 K to about 523 K.

9. The method of any one of claims 1-4, comprising reacting the levulinic acid solution at a weight-hourly space velocity of from about 0.1 hr$^{-1}$ to about 50 hr$^{-1}$.

10. The method of any one of claims 1-4, comprising reacting the levulinic acid solution at a weight-hourly space velocity of from about 0.1 hr$^{-1}$ to about 30 hr$^{-1}$.

11. The method of any one of claims 1-4, comprising reacting the levulinic acid solution at a weight-hourly space velocity of from about 0.1 hr$^{-1}$ to about 10 hr$^{-1}$.

12. The method of any one of claims 1-4, comprising reacting the levulinic acid solution at a pressure of from about 0.01 bar to about 300 bar.

13. The method of any one of claims 1-4, comprising reacting the levulinic acid solution at a pressure of from about 1 bar to about 20 bar.

14. The method of any one of claims 1-4, comprising reacting the levulinic acid solution at a pressure of from about 1 bar to about 5 bar.

15. The method of claim 1, comprising reacting the levulinic acid solution in a continuous reactor.

16. A method for converting levulinic acid to methyl vinyl ketone, the method comprising:
reacting in a continuous reactor an aqueous solution comprising levulinic acid, over a solid acid catalyst, at a temperature of from room temperature to about 600 K, and in the absence of added molecular hydrogen, a pressure of from about 0.1 bar to about 300 bar, and a weight-hourly space velocity of from about 0.1 hr$^{-1}$ to about 50 hr$^{-1}$.

17. The method of claim 16, comprising reacting the levulinic acid solution over a solid acid catalyst selected from the group consisting of ceramic acid catalysts, acidic molecular sieves, aluminosilicates, titanosilicates, borosilicates, mixed metallic oxides, phosphated metal oxides, sulfated metal oxides, acidic ion exchange resins, heteropoly acids, and combinations thereof.

18. The method of claim 16, comprising reacting the levulinic acid solution over a solid acid catalyst selected from the group consisting of aluminosilicates, titanosilicates, borosilicates, acidic zeolites, tungstated zirconia, and acidic polyoxymetalates.

19. The method of claim 16, comprising reacting the levulinic acid solution at a temperature of from about 350 K to about 600 K.

20. The method of claim 16, comprising reacting the levulinic acid solution at a temperature of from about 400 K to about 523 K.

21. The method of claim 16, comprising reacting the levulinic acid solution at a weight-hourly space velocity of from about 0.1 $hr^{-1}$ to about 30 $hr^{-1}$.

22. The method of claim 16, comprising reacting the levulinic acid solution at a weight-hourly space velocity of from about 0.1 $hr^{-1}$ to about 10 $hr^{-1}$.

23. The method of claim 16, comprising reacting the levulinic acid solution at a pressure of from about 1 bar to about 20 bar.

24. The method of claim 16, comprising reacting the levulinic acid solution at a pressure of from about 1 bar to about 5 bar.

\* \* \* \* \*